United States Patent [19]

Myers et al.

[11] 4,304,120

[45] Dec. 8, 1981

[54] AUTOMATIC GAS MEASUREMENT AND ANALYSIS FOR A TEST CELL

[76] Inventors: Tommy E. Myers, Rte. 7, Box 426X; Jonathan C. Duke, Rte. 6, Box 59 B-10, both of Vicksburg, Miss. 39180

[21] Appl. No.: 132,592

[22] Filed: Mar. 21, 1980

[51] Int. Cl.³ .............................................. G01N 7/00
[52] U.S. Cl. ................................. 73/19; 73/861.02; 73/864.73; 73/432.5 D
[58] Field of Search ................... 73/19, 198, 432.5 D, 73/421.5 R, 863.01, 863.33, 863.83, 864.73, 861.02

[56] References Cited

U.S. PATENT DOCUMENTS

| | | | |
|---|---|---|---|
| 3,029,627 | 4/1962 | Buban | 73/19 X |
| 3,247,713 | 4/1966 | Reed | 73/199 |
| 3,459,047 | 8/1969 | Sumansky | 73/421.5 R |
| 3,486,382 | 12/1969 | Res et al. | 73/421.5 A |
| 3,578,404 | 5/1971 | Walles et al. | 73/19 X |
| 3,921,457 | 11/1975 | Barnes, Jr. et al. | 73/421.5 R |
| 3,943,750 | 3/1976 | McLaughlin | 73/421.5 R X |
| 3,978,732 | 9/1976 | Dillman | 73/421.5 R |
| 4,016,759 | 4/1977 | Baker et al. | 73/204 |
| 4,020,697 | 5/1977 | Jander | 73/421.5 R |
| 4,043,195 | 8/1977 | Hunting | 73/204 |
| 4,044,612 | 8/1977 | Powell | 73/421.5 R X |
| 4,090,392 | 5/1978 | Smith et al. | 73/421.5 R |
| 4,165,630 | 8/1979 | Felder et al. | 73/421.5 A X |

*Primary Examiner*—Charles A. Ruehl
*Attorney, Agent, or Firm*—Darrell E. Hollis

[57] ABSTRACT

A method and apparatus for automatic measurement of gas flow rate and gas volume from a test cell. By this method, low rates of gas production may be measured, and means are provided to limit flow rates to maximum and minimum values measurable in a mass flowmeter. Further, data logging and computational means are shown which are used for correction and manipulation of mass flow rate data obtained.

10 Claims, 4 Drawing Figures

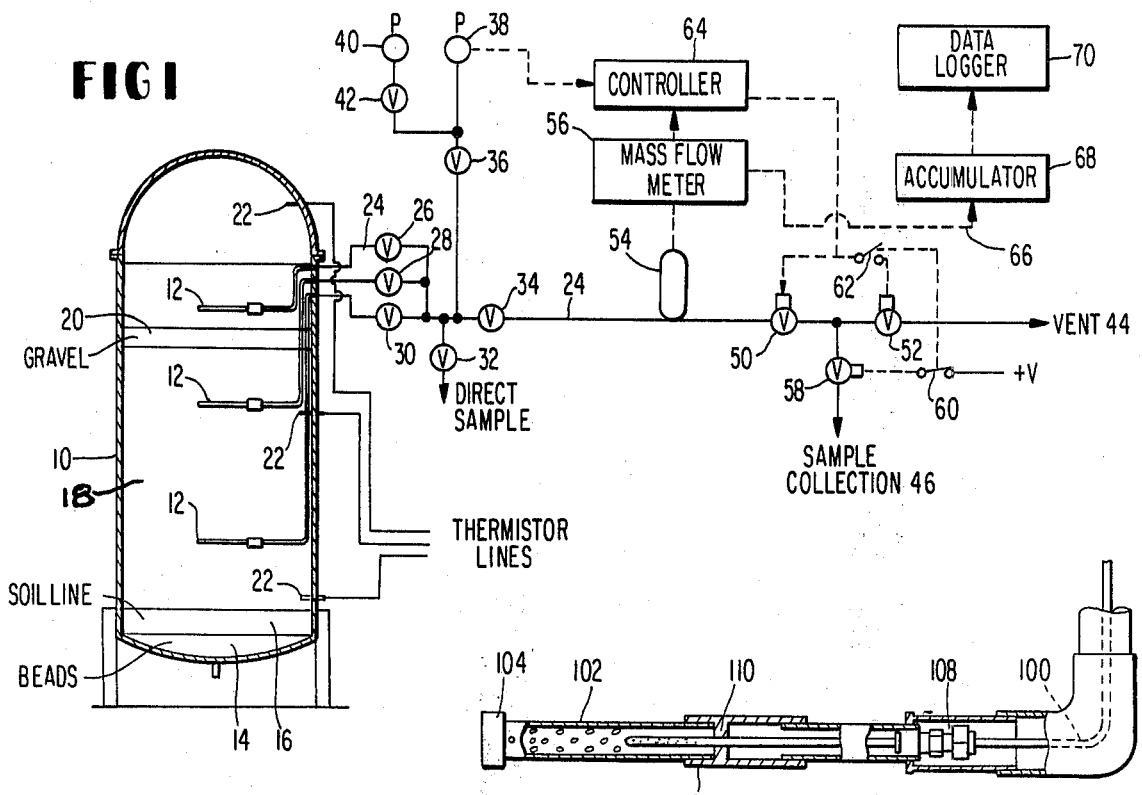
FIG 1
FIG 2
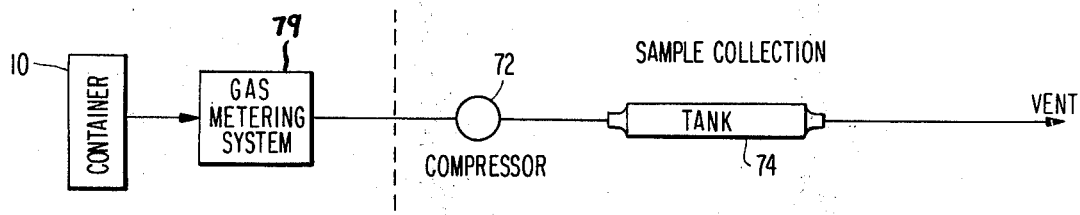
FIG 3
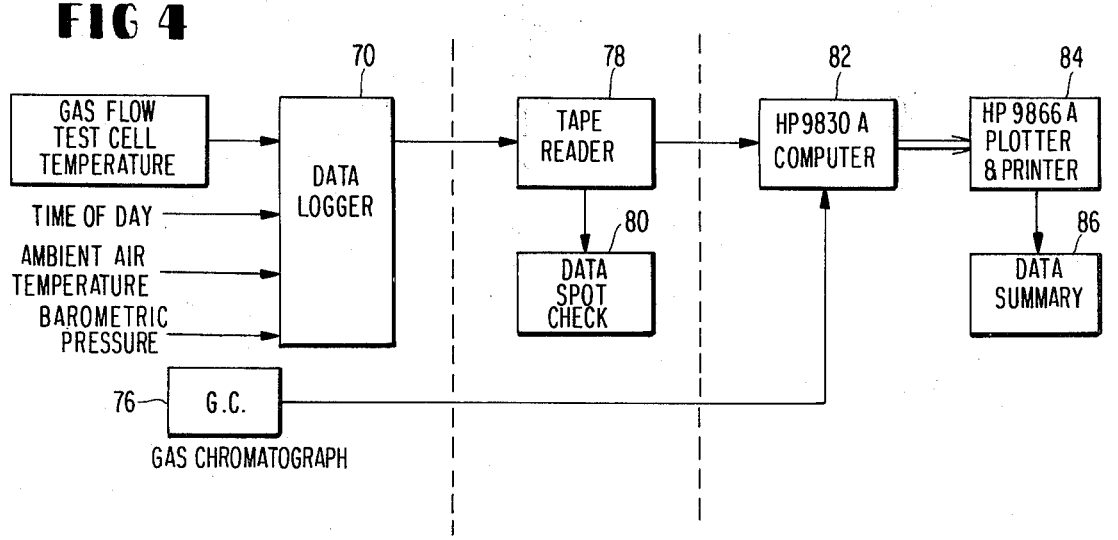
FIG 4

AUTOMATIC GAS MEASUREMENT AND ANALYSIS FOR A TEST CELL

BACKGROUND OF THE INVENTION

1. Field of the Invention

This invention relates to a method and apparatus for measuring gas flow from a test cell of the type used to analyze decomposition and gas formation to be expected from sanitary land fills containing municipal solid waste material. In such test cells, the period of time for measurement is several years and the production rate of gas may vary widely. In such test cells, the rate of gas production may at times be very low. Still further, it is necessary in such test cells to prevent any ambient air from entering the test cell during the measurement period because contamination of the gas within the cell will destroy the accurate measurement of the gas produced in the test cell.

2. Description of the Prior Art

In systems used heretofore, it has been difficult to measure the gas flow rates when the flow becomes very low because of changing temperature conditions, barometric pressure, or decreased gas production which is experienced after several years have passed during a test period.

Without an accurate automated gas monitoring system to determine the gas output from a test cell, it has been impossible to obtain consistent and accurate gas output measurements from such cells.

Gas generation in sanitary land fills creates two major problems which affect the environment. Carbon dioxide is produced by the land fill and goes into solution in the surrounding ground water and causes a "hardness halo" in the ground water near the fill. Still further, methane gas is produced, and this gas can migrate off site and create harzardous conditions in surrounding structures. Therefore, it has been necessary to accurately investigate the gas production quantity and constituency of sanitary land fills which contain municipal solid waste matter. Test cells which simulate the land fill have been built in order to obtain a more accurate measurement of composition and amount of gas produced during decomposition. It is therefore essential that accurate measurement of the gases produced by such test cells be made, in order to fully understand the pollution problem, and to further exploit the possible fuel source available from the methane gas production from such land fills.

It is this demand for accuracy which has led to the development of the invention disclosed and described herein.

OBJECTS AND SUMMARY OF THE INVENTION

The object of the present invention is for provision of a means for automatically and accurately measuring the gas flow rate, or gas volume produced in a test cell where the gas flow may vary widely, and the time of measurement is over a period of several years.

In this invention, a plurality of gas sampling means are positioned within an air-tight test cell which contains municipal solid waste. A plurality of pipes or conduit means are connected to the gas samplers, and are used to supply the gas to a pressure detecting means or pressure sensitive switch which is used to control electrical valves which vent the gas produced in the test cell either to the atmosphere, or to a sample collection container. A mass flow meter is provided in the line leading to the control valves and the vent which measures the mass rate of flow of the gas through the conduit. A data accumulator is provided which receives the information from the mass flow meter in analog form, and which stores information relating to the mass flow until such time that it is further processed by means of a data log, and further computational steps which correct the meter readings in accordance with the actual gas constituency and other parameters.

The mass flow meter also has an output connected to a controller means which is used to prevent excessive flow which would either damage or produce inaccuracies in measurement when the flow rate exceeds that which the mass flow meter is capable of measuring. When the mass flow meter output exceeds a predetermined level, the controller will limit the output flow by turning off the vent valves. The vent valves will not be turned on again until the mass flow meter senses a flow at a predetermined lower level. In this way, the mass flow meter is protected from excessive flow, and inaccuracies of measurement are avoided under conditions where the mass flow meter would run off scale or otherwise prove to be inaccurate.

This invention further includes a sample collection means which is a compressor and storage tank. The gas samples are collected periodically, and are analyzed in a gas chromatograph in order to compensate for different gases produced. This compensation is necessary so that accurate computations of the total gas output from the test cell may be made in the computational procedures which follow the actual flow measurement.

The computational procedures are essentially an adjustment of the measured gas flow rate or volume in accordance with the test cell temperatures, the ambient air temperatures, the barometric pressure, and the gas constituency itself. In this manner, very accurate data is obtained for purposes of better understanding the gas production experienced in municipal solid waste land fill areas.

DESCRIPTION OF THE DRAWINGS

FIG. 1 in the lefthand portion shows a typical test cell, and on the righthand side shows the means for measurement of the mass flow rate of the gas produced in the test cell.

FIG. 2 shows a sampling probe of the type used to detect the gas pressure within the chamber, and to allow gas flow from the chamber to the measurement and analysis apparatus.

FIG. 3 shows a typical means for gas sample collection.

FIG. 4 shows the method used to assemble the data collected, and the processing steps used to determine the precise gas production of the test cell.

DESCRIPTION OF THE PREFERRED EMBODIMENT

Referring to FIG. 1, there is shown a test cell 10 which has placed within it at several locations a plurality of gas sampling probes 12. When the test cell 10 is used to simulate municipal solid waste land fill conditions, the bottom of the tank is first filled with polypropylene beads 14, and a soil liner 16 is placed on top of the polypropylene beads 14. Immediately above the soil liner 16, a mass of municipal solid waste 18 is placed into the tank. Above the municipal solid waste 18 is placed a layer of wash-pea gravel 20. At the top of the tank, additional means are also provided for inserting water into the tank periodically in order to simulate moisture conditions encountered in a natural land fill. In addition to the gas sampling means 12, there is also provided within the tank a plurality of thermistor detection devices 22 which are used to measure the temperature within the tank.

Each of the gas sampling means 12 is connected by a pipe 100 to a group of pipes which comprise a conduit means 24 for venting the gas from the probes to atmosphere, or to a collection apparatus.

A plurality of manual control valves 26, 28 and 30 are provided so that sampling can be obtained from different areas of the tank if desired, although normal measurement is made with all probes connected to the conduit apparatus 24 for purposes of gas measurement.

If it is desired, direct samples may be taken from the tank 10 by opening valve 32. Valve 34 is provided to cut off the automatic gas measurement system when direct samples are to be taken by virtue of the opening of valve 32. Yet another valve 36 is provided between the conduit 24 and pressure detecting device 38 and pressure guage 40. The valve 36 when closed will prevent the pressure detecting means 38 from sensing any pressure produced by the test cell 10. In this manner, valve 36 serves to disable the automatic measuring system. Similarly, valve 42 is used to cut off gas to pressure guage 40.

As can be seen in FIG. 1, conduit means 24 carries the gas flow to either a vent 44 or sample collection area 46.

The differential pressure switch/guage or pressure detecting means 38 incorporates the guage 40 and switch set point indicators for continuous indication of the internal pressure and switch settings. The pressure switch/guage is a Dywer photohelic Model 3000-5-CM. This unit is diaphragm operated and switching is accomplished by photocell controlled relays. It is this pressure detecting means 38 which is used to operate two normally closed solenoid valves 50 and 52.

When the test cell pressure reaches the high set point, the two solenoid valves 50 and 52 open and gas from the test cell 10 passes through the conduit 24 and through the mass flow meter detector 54, 56, through valves 50 and 52 and to the atmospheric vent 44. When the pressure drops to below the low set point of the pressure detecting means 38, the solenoid valves close.

The separate pressure guage 40 has also been installed to sense the pressure in the conduit 24. This separate guage 40 provides a convenient periodic check on the pressure detecting means 38 and its performance.

The linear gas flow meter 54, 56 consists of an electrically-heated tube, and an arrangement of thermocouples, which measures the differential cooling caused by the gas passing through the tube. Thermal electric elements generate D.C. voltages which are directly proportional to the rate of mass flow of gas through the tube. This proportionality permits the linear gas flow meter to be calibrated if gas composition and thermal conductivity of the component gases are known. The mass flow meter itself, however, is insensitive to ambient pressure and temperature changes. The mass flow meter used in the preferred embodiment has a maximum flow rate of one liter per minute and generates a 5 volt D.C. output. The flowmeter used is a Matheson Model 8116-0113 with associated Model H-1K transducers.

Connected between the pressure detecting means 38 and the valves 50 and 52 is a controller 64. Controller 64 is a solid state logic box which operates the solenoid valves 50 and 52 in response to both the mass flow meter 54, 56 and the pressure detecting means 38. When the pressure within the test cell reaches the high set point of the pressure detecting means, solenoid valve means 50 and 52 open and gas moves out of the test cell and through the flowmeter 54, 56. When and if the flow rate reaches 95% of the measuring capacity of the flowmeter 54, 56, solenoid valve 52 will close in order to keep the gas flow within the measurable range of the instrument 54, 56. When the flow rate drops to 20% of the capacity of the mass flow detector 54, 56, solenoid valve 52 will again re-open. By this method, the gas flow rate is prevented from exceeding the range of the gas flowmeter 54, 56. When the gas flow from the test cell 10 exceeds the maximum, the pressure sensed by the detecting means 38 will remain high, possibly higher than the high set point. The flow rate, however, is reduced through the action of valve 52, the controller 64, and the mass flowmeter. The valve 52 will essentially cut on and off rapidly, thereby reducing the overall flow through conduit 24 to a measurable amount. The valve 52 chatters as it turns on and off. Valves 50 and 52 remain activated until the pressure drops to a low set point of the pressure detecting means 38. When the low set point is reached, both solenoid valves 50 and 52 are then closed and remain closed until such time as the pressure builds up to the high set point of the pressure detecting means 38.

The mass flowmeter also has an output 66 which is an analog signal. This signal is received by an accumulator 68 where it is digitized and accumulated in an electronic counter. The counts from the accumulator counter 68 are then recorded on a cassette tape at hourly intervals by a 56 channel, Martek DLS Data Logger 70.

The counter registers of the accumulator 68 are returned to zero after each hourly update. With each update, the data logger 70 also records the day, the hour (from an internal clock), the temperatures from the thermistor locations in the test cell 10, the barometric pressure, the ambient air temperature from two locations in the test cell area, and other reference voltages for the electronics associated with the temperature measurement. All data logged in the logger 70 are identified in accordance with day and hour.

In FIG. 3, there is shown schematically the gas sample collection system. In order to properly compute the mass rate of flow and the total flow, as noted above, it is necessary to know the content of the mixture of gases, or the gas constituency of the test cell 10 output. Therefore, it is necessary to periodically collect samples of the gas for further testing in a gas chromatograph 76 for the purpose of determining the type of gases being emitted from the test cell 10. Referring again to FIG. 3, there is shown a compressor 72 which receives gas samples from valve 58 associated with the gas metering system 79. The compressor 72 forces the gases into tank 74 for collection, and subsequent testing in chromatograph 76.

Gas sample collection is not automatic, but is accomplished at periodic intervals by manual means. When it is desired to collect a gas sample, a double pole/double throw switch 60, 62 is switched. By this switch, valve means 52 is disconnected and hence turned off; and valve means 58 is connected to the controller 64 and hence turned on when the pressure and flow conditions are such that an output is received from controller 64. In this way, sample collection can be made while the system is operating in its normal fashion. Once sample collection is complete, double pull/double throw switch 60, 62 will be returned to its normal position, and the gases merely vented to the atmosphere by means of vent 44.

A sample once collected is associated with a particular mass of data accumulated in data logger 70. As noted, above data logger 70 receives as inputs gas flow information, test cell temperature, time of day of the information, ambient air temperature, and barometric pressure. The output of data logger 70 is fed to a tape reader 78, and a spot check device 80 is used to ascertain the reasonableness of the data received. The output of the tape reader 78 is fed to a computer which is a Hewlett Pakcard HP9830A computer. This computer then computes the gas production of the test cell as corrected by the information from the gas chromatograph 76 to produce a plot in a Hewlett Packard HP9866A plotter and printer of the gas production received from the test cell.

The computer 82 is a Hewlett Pakcard 9830A computer, the plotter and printer 84 is a Hewlett Packard 9866A plotter and printer, and the data summary device 86 is used to record the data as processed by the computer 84.

The gas chromatograph 76 used herein is a Perkin-Elmer Sigma 3 gas chromatograph which senses oxygen, hydrogen, nitrogen, carbon dioxide, methane and water vapor. This device is calibrated with commercially prepared gas mixtures, and the results are reported in volume percent.

The operation of the data reduction system shown in FIG. 4 is as follows: The raw data tapes from the logger 70 are read by a Martek Model 421-DRS magnetic tape reader 78 and printed on an Anadex Model DP-500-9 tape printer 80. A second Martex Model 421-DRS magnetic tape reader (78) is used to transfer the data from the magnetic tape to a Hewlett Packard Model 9830A computer (82) through a Martek Model 421-12 DRS computer interfacing unit. The data fed from the tapes to the computer 82 is immediately printed on printer 84 at which time it is verified by comparison with the print-out from the Anadex unit or spot check 80. After verification, the data is reorganized and stored on magnetic tapes in raw form or in an array that allows for easy access and manipulation by the computer 82. As the raw data tapes become available, they are reduced to engineering units by the computer 82 which uses equations which correct for non-linear output from the thermistors, barometric pressure sensors, and for variation in gas composition as determined by the chromatograph 76. The reduced data for an operating day is stored on a new tape file along with the cumulative gas production for the operating day. In this manner, the computer 82 builds a tape file library for the test cell 10.

The computer 82 is also used to compute a plot of time versus gas production, temperature, and barometric pressure for a test cell 10 on each day. Another program has also been developed to plot the daily cumulative gas production over longer periods of time.

Obviously the computer can be programmed to perform other data manipulations as needed from the data in reduced form which has been obtained from the test cell.

Referring now to FIG. 2, there is shown a gas sampling probe of the type used in the preferred embodiment. This gas probe has a copper tube 100 which is coated both inside and out with a coal tar epoxy mixture in order to prevent corrosion by the material or the leachate within the test cell. This copper tubing 100 is fitted into a perforated PVC pipe 102 which has a cap 104 at its end. The purpose of the perforated PVC pipe is merely to protect the tubing during compaction of the municipal solid waste placed within the test cell 10. The copper tube portion 106 within the test cell is connected by means of a coupling 108 to copper tube 100 which transmits the gas to the conduit means 24.

An epoxy sealed rubber insert 110 is placed upstream from the coupling 108 in order to prevent leachate contact with the union and consequent corrosion of the union 108. Exterior to the tank there is a PVC pipe 112 which is provided for further protection of the gas transmission copper tube 110 outside of the tank.

Obviously, numerous modifications and variations of the present invention are possible in light of the above teachings. It is therefore to be understood that within the scope of the appended claims the invention may be practiced otherwise than as specifically described herein.

I claim as my invention:

1. Apparatus for measuring gas production in a test cell, comprising:
   a. means for sampling gas located within said test cell;
   b. conduit means connected to receive the gas output of said gas sampling means;
   c. means connected to said conduit means for detecting the pressure in said test cell and for producing an electrical output signal in response to the detected test cell pressure;
   d. valve means connected to said conduit means and responsive to said electrical output signal for venting said gas output when said detected test cell pressure exceeds a predetermined value;
   e. means for measuring the rate of mass flow of said gas output when said valve means vents said gas output; and
   f. means connected to receive the output from said mass flow measuring means for accumulating and storing the rate of mass flow measured.

2. The apparatus of claim 1, further including means responsive to said output signal and to said output from said mass flow measuring means for producing a control signal for opening said valve means when said detected test cell pressure exceeds a first predetermined level, for closing said valve means when said pressure is reduced to a second predetermined level, and for closing said valve means when said rate of mass flow exceeds a predetermined maximum level, and re-opening said valve means when said rate of mass flow is reduced to a predetermined minimum level.

3. The apparatus of claims 1 or 2, further including means for collecting a sample of said gas output.

4. The apparatus of claim 2, further including means for collecting a sample of said gas output which includes valve means controlled by said pressure detecting means for taking a sample of said output gas.

5. The apparatus of claim 4, further including data logger means for recording gas flow and gas temperature of said output gas, ambient air temperature and barometric pressure.

6. The apparatus of claim 5, further including means for detecting the constituency of said output gas in said sample collecting means.

7. The apparatus of claim 6, further including means for computing the total gas flow from said test cell as a function of said measurement rate of mass flow and gas temperature of said output gas, and ambient air temperature, and barometric pressure.

8. The apparatus of claim 1, further including manual control valve means associated with said conduit means for selectively cutting off said gas sampling means to prevent direct sampling of said output gas.

9. A method of measuring the rate and quantity of gas flow from a test cell over a period of time, comprising the steps of:
 a. placing a gas sampling probe within said test cell;
 b. venting the output gas from said sampling probe when the pressure difference between said test cell and the barometric pressure exceeds a predetermined maximum;
 c. stopping said venting when the pressure difference between said test cell and the barometric pressure falls below a predetermined minimum;
 d. measuring the mass flow during the time when said gas is vented; and
 e. accumulating the mass flow measurements for further data manipulation.

10. The method of claim 9, further including the steps of
 f. periodically collecting samples of said output gas and determining its constituency;
 g. correcting the measurement of the mass flow measurement in accordance with the barometric pressure, the ambient air temperature, the test cell temperature, the time of measurement, and the constituency of said output gas.

* * * * *